United States Patent [19]

Schwager

[11] Patent Number: 5,788,654
[45] Date of Patent: Aug. 4, 1998

[54] WEDGE-TIPPED CATHETER GUIDEWIRE

[75] Inventor: Michael Schwager, Winterthur, Switzerland

[73] Assignee: Schneider (Europe) A.G., Bulach, Switzerland

[21] Appl. No.: 674,369

[22] Filed: Jul. 2, 1996

[30] Foreign Application Priority Data

Jul. 18, 1995 [EP] European Pat. Off. ............ 95111243

[51] Int. Cl.$^6$ ............................................ A61B 5/00
[52] U.S. Cl. ...................... 600/585; 604/95; 604/280
[58] Field of Search ........................... 128/772, 657, 128/658; 604/95, 96, 280, 281, 282, 283

[56] References Cited

U.S. PATENT DOCUMENTS

| | | | |
|---|---|---|---|
| 4,003,369 | 1/1977 | Heilman et al. | 128/2 |
| 4,080,706 | 3/1978 | Heilman et al. | 29/173 |
| 4,545,390 | 10/1985 | Leary | 128/772 |
| 4,724,846 | 2/1988 | Evans, III. | 128/772 |
| 4,779,628 | 10/1988 | Machek | 128/772 |
| 4,846,186 | 7/1989 | Box et al. | 128/657 |
| 4,854,330 | 8/1989 | Evans, III. et al. | 128/772 |
| 4,895,168 | 1/1990 | Machek | 128/772 |
| 5,067,489 | 11/1991 | Lind | 128/772 |
| 5,127,917 | 7/1992 | Niederhauser et al. | 606/191 |
| 5,154,705 | 10/1992 | Fleischhacker et al. | 604/282 |
| 5,165,421 | 11/1992 | Fleischhacker et al. | 128/772 |
| 5,217,026 | 6/1993 | Stoy et al. | 128/772 |
| 5,228,453 | 7/1993 | Sepetka | 128/772 |
| 5,230,348 | 7/1993 | Ishibe et al. | 128/772 |
| 5,234,003 | 8/1993 | Hall | 128/772 |
| 5,238,004 | 8/1993 | Sahatjian et al. | 128/772 |
| 5,243,996 | 9/1993 | Hall | 128/772 |
| 5,341,818 | 8/1994 | Abrams et al. | 128/772 |
| 5,363,861 | 11/1994 | Edwards et al. | 128/772 |
| 5,365,942 | 11/1994 | Shank | 128/772 |
| 5,365,943 | 11/1994 | Jansen | 128/772 |
| 5,368,049 | 11/1994 | Raman et al. | 128/772 |
| 5,372,144 | 12/1994 | Mortier et al. | 128/772 |
| 5,402,799 | 4/1995 | Colon et al. | 128/772 |
| 5,404,886 | 4/1995 | Vance | 128/772 |
| 5,409,015 | 4/1995 | Palermo | 128/772 |
| 5,427,118 | 6/1995 | Nita et al. | 128/772 |
| 5,429,139 | 7/1995 | Sauter | 128/772 |
| 5,433,200 | 7/1995 | Fleischhacker, Jr. | 128/657 |
| 5,443,455 | 8/1995 | Hergenrother et al. | 428/380 |
| 5,443,907 | 8/1995 | Slaikeu et al. | 428/375 |
| 5,465,732 | 11/1995 | Abele | 128/772 |
| 5,497,783 | 3/1996 | Urick et al. | 128/772 |
| 5,497,786 | 3/1996 | Urick | 128/772 |
| 5,507,301 | 4/1996 | Wasicek et al. | 128/772 |
| 5,511,559 | 4/1996 | Vance | 128/772 |
| 5,520,194 | 5/1996 | Miyata et al. | 128/772 |
| 5,527,298 | 6/1996 | Vance et al. | 604/280 |
| 5,546,948 | 8/1996 | Hamm et al. | 128/662.06 |
| 5,558,101 | 9/1996 | Brooks et al. | 728/772 |
| 5,588,443 | 12/1996 | Davidson | 128/772 |
| 5,605,163 | 2/1997 | Hani | 128/772 |
| 5,606,979 | 3/1997 | Hodgson | 128/772 |
| 5,617,875 | 4/1997 | Schwager | 128/772 |
| 5,622,184 | 4/1997 | Ashby et al. | 128/772 |

FOREIGN PATENT DOCUMENTS

| | | |
|---|---|---|
| 0279959A1 | 8/1988 | European Pat. Off. . |
| 0495299A1 | 7/1992 | European Pat. Off. . |
| 9410907 | 5/1994 | WIPO . |

OTHER PUBLICATIONS

European Search Report in EP 95111243.2 filed Jul. 18, 1995, together with communication and one–page Annex.

*Primary Examiner*—Max Hindenburg
*Assistant Examiner*—Pamela L. Wingood
*Attorney, Agent, or Firm*—Peter C. Richardson; Lawrence C. Akers; Philip C. Strassburger

[57] ABSTRACT

A catheter guide wire comprises a main section having a circular cross-section and a distal end section surrounded by a spiral. The distal end section has a portion adjoining the guide wire tip, in the shape of a wedge, the height of which diminishes towards the guide wire tip and the width of which increases towards the guide wire tip.

9 Claims, 3 Drawing Sheets

WEDGE-TIPPED CATHETER GUIDEWIRE

BACKGROUND OF THE INVENTION

This invention concerns a catheter guide wire with a main section that has a circular cross section and a wedge-shaped distal end section.

European Patent A 279,959 discloses a catheter guide wire whose end section has a diameter that is reduced in stages toward the tip of the guide wire. The guide wire is flattened in the area next to the tip of the guide wire, where it has a rectangular cross section with a uniform width and thickness. The purpose of this gradual reduction in diameter in the direction of the tip of the guide wire is to improve the flexibility of the wire in this area. However, the design must always assure that despite the reduction in diameter, a torque applied at the proximal end of the guide wire will be transmitted to the distal end area of the guide wire so the wire can still be controlled during use. Because of the torque transmitting requirement and also for strength reasons, the diameter of the guide wire at the tip of the wire cannot be reduced to an unlimited extent. Flattening of the section closest to the tip of the guide wire has been employed instead of a reduction in diameter. This flattening yields a great flexibility without having an excessive influence on the formability of the tip or the transmission of torque. There is a drastic change in flexibility at the transition point between the reduced-diameter area and the flat section at the tip of the guide wire, and the flexibility then remains constant in the entire flat area. Strength problems may also occur at this transition point. The foregoing document is incorporated herein, in its entirety, for all purposes.

SUMMARY OF THE INVENTION

The object of this invention is to create a catheter guide wire that will have a great flexibility in the area of its tip while maintaining its formability as well as its ability to transmit torque without any loss or strength.

This object is achieved according to this invention by the fact that the area of the distal end section closest to the tip of the guide wire is in the shape of a wedge with a height that decreases toward the tip of the guide wire and a width that increases toward the tip of the guide wire.

In sum, the present invention relates to a catheter guidewire with a main section having a circular cross-section and a distal end section surrounded by a spiral, wherein the distal end section has a portion, adjoining the guidewire tip, in the shape of a wedge, the height of which diminishes towards the guidewire tip and the width of which increases towards the guidewire tip. The end section between the main section and the wedge-shaped portion may have at least one portion having a reduced circular cross-section, the height and width of the wedge at its proximal end corresponding to the diameter of the portion adjoining in the proximal direction and said distal end of said wedge being the tip of the guide wire.

The present invention also relates to a catheter guidewire adapted for use with an intravascular catheter such as an angioplasty catheter. The guidewire has a main portion and a distal portion, wherein the main portion has a substantially circular cross-section and the distal portion has a wedge-shaped element. The distal portion has a tip and the wedge-shaped element may have a height that decreases toward the tip. The wedge-shaped element may have a width that increases toward the tip. The distal portion may further comprise a metal helical coil surrounding the wedge-shaped element.

On the basis of this design of the catheter guide wire according to this invention, there is a steady increase in flexibility in the area adjacent to the tip of the guide wire without any negative effects on the other requirements regarding the behavior of the end section of the guide wire.

BRIEF DESCRIPTION OF THE DRAWINGS

This invention will now be illustrated in greater detail on the basis of the figures, which show the following.

DETAILED DESCRIPTION OF THE INVENTION

Figure 1:
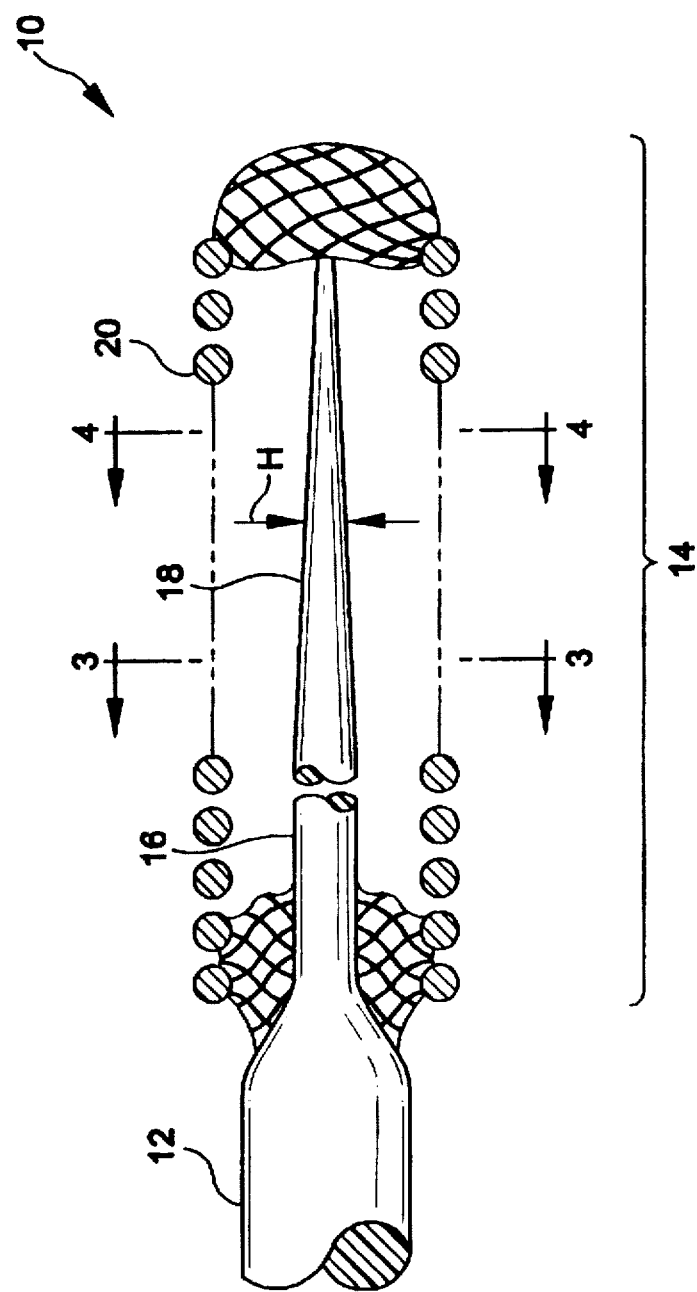
FIG. 1 shows a view of the end section of a catheter guide wire according to this invention, where the area designed to be wedge-shaped is shown from the side.

Guide wire 10, illustrated in FIG. 1, has a main section 12, only a small portion of which is shown here. Main section 12 has a circular cross section. This main section is followed by an end section 14 consisting of an area 16 with a reduced circular cross section and an area 18 in the form of a wedge adjacent to the tip of the guide wire. The height H of the wedge decreases toward the tip of the guide wire while its width B increases. The entire end section 14 is surrounded by a spiral 20 that is permanently attached to the guide wire by gluing, soldering, etc., at the tip of the guide wire and in the area of the transition between main section 12 and end section 14.

Figure 2:
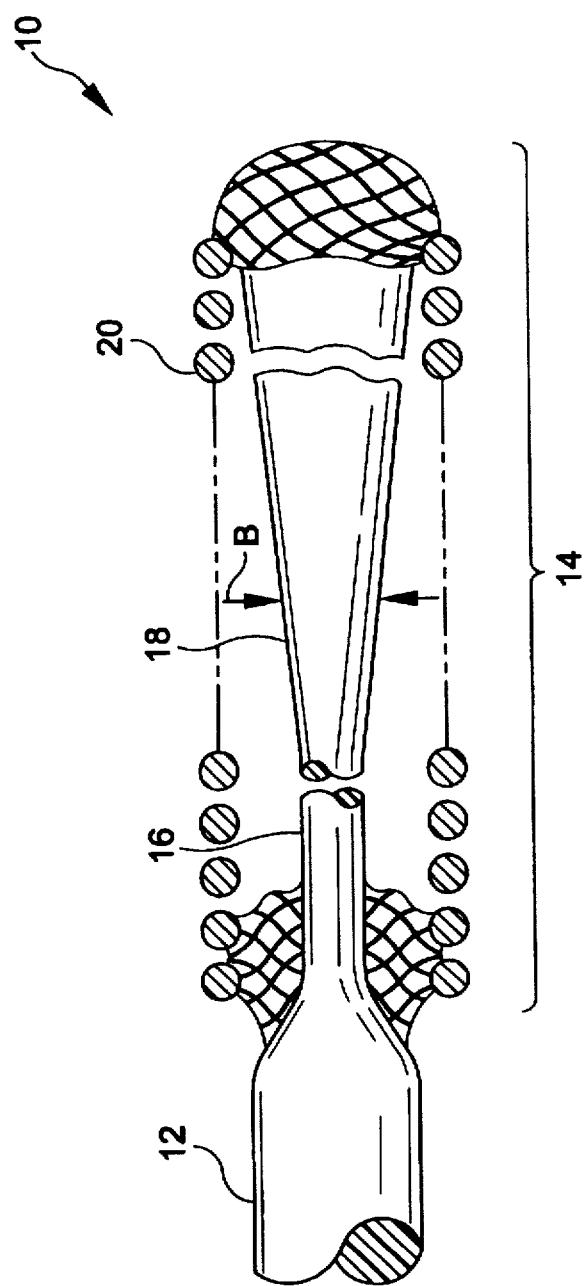
FIG. 2 shows a view of the end section of the catheter guide wire from FIG. 1 with a top view of the wedge-shaped area.
Figure 4:
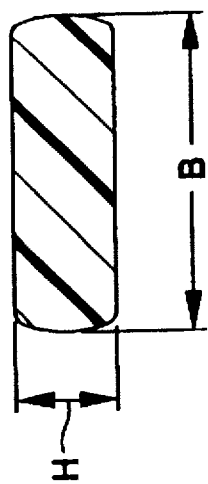
FIG. 4 shows a cross-sectional view taken at A'—A' of FIG. 1.
Figure 3:
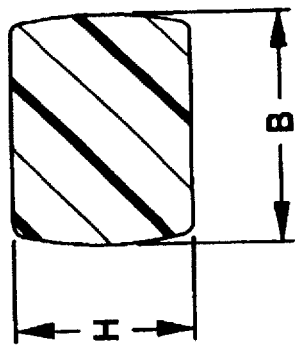
FIG. 3 shows a cross-sectional view taken at A—A of FIG. 1.

FIGS. 1 and 2 show that in end section 14 there is a smooth transition between area 16, which has a reduced circular cross section, and wedge-shaped area 18. In this transition area the height and width of the wedge at its proximal end thus correspond to the diameter of area 16. Due to the wedge-shaped design of area 18, end area 14 is thus always more flexible toward the tip of the guide wire because there is a continuous decline in wedge height H. Because of this smooth transition between area 16, which has a reduced circular cross section, and wedge-shaped area 18, there are no negative effects on strength in the transition between these two areas. In particular, there is no susceptibility to buckling in this transition area, and maximum control of the movement of the tip of the guide wire is maintained. Another advantage of the smooth transition is that no variations in rigidity are apparent when the guide wire is supported on the vascular wall in advancing the guide wire through areas with narrow curves in the blood vessels.

This invention has been described herein in detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

I claim:

1. A catheter guidewire comprising a main section having a circular cross-section and a distal end section surrounded by a spiral, wherein said distal end section has a portion, adjoining the guidewire tip, in the shape of a wedge, the height of which diminishes towards the guidewire tip and the width of which increases towards the guidewire tip.

2. The catheter guidewire of claim 1, wherein said end section between said main section and said wedge-shaped portion comprises at least one portion having a reduced circular cross-section, the height and width of the wedge at its proximal end corresponding to the diameter of said portion adjoining in the proximal direction and said distal end of said wedge being the tip of the guide wire.

3. A catheter guidewire adapted for use with an intravascular catheter such as an angioplasty catheter, the guidewire comprising a main portion and a distal portion, the main portion including a substantially circular cross-section and the distal portion including a wedge-shaped element, the wedge-shaped element having a height and width wherein one of the height or the width increases distally along at least a portion of the distal portion.

4. The catheter of claim 3 wherein the distal portion has a tip and the wedge-shaped element has a height that decreases toward the tip.

5. A catheter guidewire comprising:

a core element including a proximal portion and a distal portion, the proximal portion of the core element comprising a substantially circular cross-section and the distal portion of the core element comprising a wedge-shaped region wherein the wedge-shaped region has a height that decreases distally and a width that increases distally along at least a portion of the distal portion.

6. The catheter guidewire of claim 5 wherein the distal portion of the core element further comprises a metal helical coil surrounding the wedge-shaped element.

7. A catheter guidewire of claim 5 wherein the core element is substantially straight.

8. A catheter guidewire of claim 7 wherein the guidewire is substantially straight.

9. A catheter guidewire of claim 5 wherein the distal portion has a tip.

* * * * *